US012797211B2

(12) United States Patent
Teng et al.

(10) Patent No.: US 12,797,211 B2
(45) Date of Patent: Nov. 17, 2026

(54) COMBINED TESTBENCH TYPE AND WALKING TYPE COMPLIANT EXOSKELETON SYSTEM

(71) Applicant: The Hong Kong Polytechnic University, Hung Hom (HK)

(72) Inventors: Long Teng, Hung Hom (HK); Lin Liu, Hung Hom (HK)

(73) Assignee: The Hong Kong Polytechnic University, Hung Hom (HK)

( * ) Notice: Subject to any disclaimer, the term of this patent is extended or adjusted under 35 U.S.C. 154(b) by 799 days.

(21) Appl. No.: 18/132,011

(22) Filed: Apr. 7, 2023

(65) Prior Publication Data

US 2024/0335301 A1 Oct. 10, 2024

(51) Int. Cl.
*A61F 2/64* (2006.01)
*A61F 2/66* (2006.01)
*A61F 2/70* (2006.01)

(52) U.S. Cl.
CPC .............. *A61F 2/64* (2013.01); *A61F 2/6607* (2013.01); *A61F 2/70* (2013.01)

(58) Field of Classification Search
CPC .................. A61H 3/00; A61H 2201/12; A61H 2201/1207; A61H 2201/1215; A61H 2201/14; A61H 2201/1436; A61H 2201/1481; A61H 1/0237–0288; B25J 9/0006; A61F 2002/5007; A61F 2002/5009; A61F 2002/5072–5079; A61F 2002/6836; A61F 2002/663
See application file for complete search history.

(56) References Cited

U.S. PATENT DOCUMENTS

2007/0123997 A1* 5/2007 Herr .......................... A61F 2/60 602/23
2018/0325713 A1* 11/2018 Gregg ................... A61F 5/0102
2020/0352811 A1* 11/2020 Varghese ................. A61H 1/02
2021/0122040 A1* 4/2021 Lefeber .................. B25J 13/085
2021/0369533 A1* 12/2021 Huang ................... B25J 9/0006
(Continued)

FOREIGN PATENT DOCUMENTS

CN 110522600 A * 12/2019 ............... G01L 5/00
KR 101588281 B1 * 2/2016 ............... A61H 1/02

OTHER PUBLICATIONS

Machine translation of CN-110522600-A. Accessed from PE2E tool on Jan. 2026. (Year: 2019).*
(Continued)

*Primary Examiner* — Joseph D. Boecker
*Assistant Examiner* — Jaeick Jang
(74) *Attorney, Agent, or Firm* — Stein IP, LLC

(57) ABSTRACT

A combined testbench type and walking type compliant exoskeleton system quickly and efficiently converts from a fixed testbench configuration to a mobile orthosis configuration. The addition of a series elastic actuator allows the combined testbench type and walking type compliant exoskeleton system to have a higher level of safe physical human-robot interaction and safety for users with spasticity or tremor. Alternate embodiments incorporating a combination of the rigid and compliant joints, allowing the combination of a swing test and enhancement of a user's strength for walking or other movement is also disclosed.

17 Claims, 5 Drawing Sheets

(56) References Cited

U.S. PATENT DOCUMENTS

2024/0116169 A1 * 4/2024 Su ............................ A61H 3/00

OTHER PUBLICATIONS

Tiboni et al. “Sensors and Actuation Technologies in Exoskeleton”, p. 26,32-33, Jun. 2022 (Year: 2022).*
Machine translation of KR-101588281-B1. Accessed from PE2E Search. (Year: 2016).*
Zhang et al. (Design and Validation of a Lightweight Hip Exoskeleton Driven by Series Elastic Actuator With Two-Motor Variable Speed Transmission, https://ieeexplore.ieee.org/stamp/stamp.jsp?amnumber=9865983. Aug. 24, 222) (Year: 2022).*
Chiu et al. (Design of a Hip Exoskeleton With Actuation in Frontal and Sagittal Planes, https://ieeexplore.ieee.org/stamp/stamp.jsp?tp=&arnumber=9452040. Aug. 2021). (Year: 2021).*
N.G. Tsagarakis, et al., “A Compact Soft Actuator Unit for Small Scale Human Friendly Robots”, IEEE International Conference on Robotics and Automation, 2009.
O. S. Al-Dahiree, et al., “Design of a Compact Energy Storage with Rotary Series Elastic Actuator for Lumbar Support Exoskeleton”, Machines, 2022.
G. Aguirre-Ollinger, et al., “Inertia Compensation Control of a One-Degree-of-Freedom Exoskeleton for Lower-Limb Assistance: Initial Experiments”, IEEE Transactions on Neural Systems and Rehabilitation Engineering, 2012.

* cited by examiner

COMBINED TESTBENCH TYPE AND WALKING TYPE COMPLIANT EXOSKELETON SYSTEM

1. FIELD OF THE INVENTION

The present invention, titled COMBINED TESTBENCH TYPE AND WALKING TYPE COMPLIANT EXOSKELETON SYSTEM, but referred to for brevity as the "Exoskeleton System," hereafter, relates to multi-purpose exoskeletal hardware and associated monitoring/control software systems. For purposes of this application, "Exoskeleton System" means the present invention: "exoskeletal systems" means examples of the field in general.

2. DESCRIPTION OF THE RELATED ART

Exoskeletal systems are known in the art: they are popular in fictional works as well as being the subject of many different real-world research projects and applications.

Historically, exoskeletal systems have been developed with single uses in mind, and either as experimental prototypes or as potential production models. Exoskeletal systems require a great deal of monitoring, feedback, and customization as they must work with a variety of users in a variety of situations. As with most complex hardware systems, prototyping and development systems usually are very different from production or use-model systems. It would be a useful invention to provide an exoskeletal system which allowed testing/experimentation during the initial development, customization, or fitting of such a system, but could quickly and efficiently be converted to an end-user model once sufficient data has been gathered and suitable customization and fitting made.

Some uses for exoskeletal systems involve being affixed to a stationary platform or "testbench," which allows them to be carefully monitored and controlled during testing or fitting of exoskeletal systems for users. Other uses involve being affixed directly to the user to provide rehabilitation therapy, diagnostic measurements, or enhancement of the natural range and power of motion of the user's movement. These uses typically require very divergent configurations of the exoskeletal systems. An exoskeletal system which allowed easy conversion from fixed testbench usage to mobile user functions would be a useful invention.

Furthermore, many exoskeletal systems are useful for patients who need physical therapy and/or physical augmentation to walk, move their arms, or perform other actions which age, injury, or disease may have caused reduced ability in such activities. Some exoskeletal systems have rigid joints to provide maximum strength and durability: others use elastic actuators to provide shock-reduction and safe physical Human-Robot Interaction ("pHRI.") An exoskeletal system which combined the benefits of both types of actuators along with the other advantages discussed above would be a useful invention.

The present invention addresses these concerns.

SUMMARY OF THE INVENTION

The present invention provides an Exoskeleton System which allows the quick and easy addition of an elastic actuator in combination with a rigid motor-driven joint.

According to an embodiment of the present invention, a combined testbench type and walking type compliant exoskeleton system comprises: a motor; a gearbox operably affixed to the motor; a lower leg member operably affixed to the gearbox via a drive member; and a magnetic encoder operably affixed to at least one of the motor, the gearbox the lower leg member, or the drive member, such that the magnetic encoder can measure the speed and/or the range of motion of the lower leg member.

According to another embodiment, a combined testbench type and walking type compliant exoskeleton system comprises: a motor; a gearbox operably affixed to the motor; a lower leg member operably affixed to the gearbox via a drive member; a series elastic actuator casing having an interior and an exterior; at least two rotating elements, each rotating element having first and second elastic member interfaces, the rotating elements operably affixed to the interior of the series elastic actuator casing such that each of the rotating elements are pivotable toward or away from one or more of the other rotating elements; and at least two elastic members, such that the elastic members operably connect the elastic member interfaces of the rotating elements, wherein torque applied to the exterior of the casing by any of the motor, the gearbox, the drive member, or the lower leg member is dampened by the elastic members via the rotating members affixed to the interior of the casing.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1B:
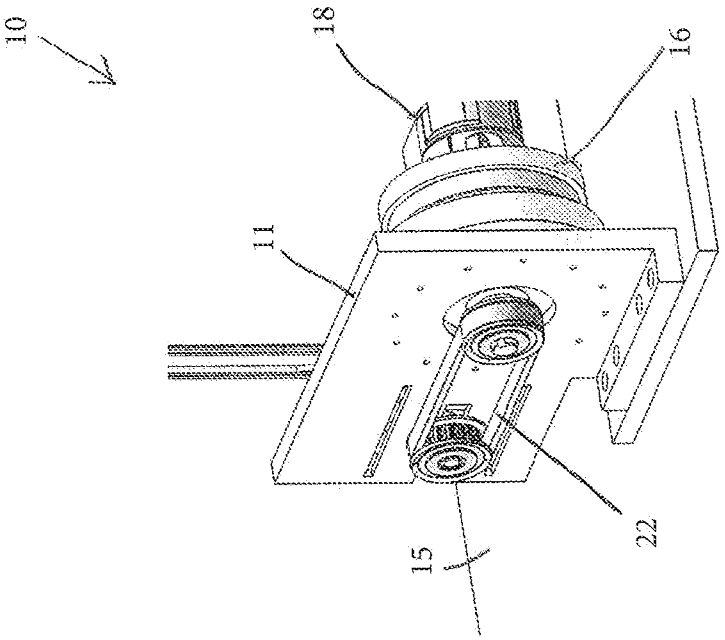
FIG. 1B is a second perspective view of the joint element of the Exoskeletal System affixed to a testbench.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, can be used with respect to the drawings. These and similar directional terms are not to be construed to limit the scope of the invention in any manner. The words attach, connect, couple, and similar terms with their inflectional morphemes do not necessarily denote direct or intermediate connections, but can also include connections through mediate elements or devices.

Though useful for many applications, the invention will be described as an Exoskeleton System intended for use by a patient (hereafter the "user,") with a condition which indicates the use of an exoskeletal system configured as either a testbench leg-swing exoskeleton or a hip orthosis. It will be apparent to persons of ordinary skill in the art that the Exoskeleton System can also be used in therapy for other health conditions or in any other suitable application that indicates the use of an exoskeletal system. It should be noted that while the primary exoskeletal members will be described as "leg" members, the Exoskeletal System could also be configured for use with the arms, the back, or any other portion of the body which can flex and is subject to loss of movement due to age, injury, or disease. For purposes of this application "leg members" includes substantially similar members meant to interface with flexible portions of the body in a substantially similar fashion.

Figure 1A:
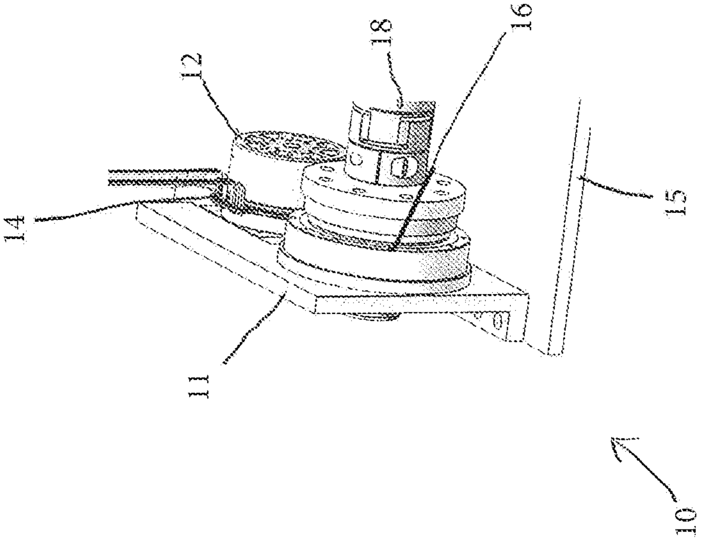
FIG. 1A is a perspective view of a joint element of the Exoskeletal System affixed to a testbench.

By referring to the provided drawings, the Exoskeleton System can be easily understood. FIG. 1A shows a closeup view of a knee exoskeletal joint as incorporated into the present invention, configured as a "leg-swing exoskeleton." Knee exoskeletal joint 10, affixed to testbench 15, includes knee joint plate 11, knee motor 12, knee magnetic encoder 14, knee gearbox 16, and drive member 18. FIG. 1B shows the reverse of the exoskeletal joint of FIG. 1A. When knee motor 12 is activated, it drives knee gearbox 16 by means of belt drive linkage 22. As will be apparent to those of ordinary skill in the art, the linkage could comprise a gear train, a chain drive, a reciprocating rod, or any other suitable linkage.

It is preferred, but not required, to use a brushless DC motor for maximum efficiency and controllability. It is likewise preferred, but not required, to use a Harmonic Drive to connect the motor (through the linkage) to the lower leg member. An optional torque sensor (NOT SHOWN, see FIGS. 3, 4, & 5) can be used to measure the interaction torque between the actuator and the load.

When knee gearbox 16 is driven by knee motor 12 via belt drive linkage 22, it rotates drive member 18. Drive member 18 is attached to a lower leg member which parallels the user's lower leg (NOT SHOWN: See FIG. 1D.) The lower leg member then pivots, drawing the user's lower leg, ankle, and foot, forward or backwards as necessary to produce the proper gait and/or to enhance the user's natural strength to move the leg and produce a walking motion. As will be made clear, this configuration can also allow evaluation of the speed and strength of the user's natural muscle movements and even provide therapeutic benefits to strengthen them. As shown, the Exoskeletal System is affixed to the testbench 15, so that a user may insert their leg and perform diagnostic evaluations and/or receive therapy through controlled motion in a controlled environment.

Knee magnetic encoder 14 measures the speed and range of motion of knee exoskeletal joint 10, and can be used to both diagnose the strength/speed of the user's motion, and to provide feedback to direct the amount of power delivered by knee motor 12.

Figure 1D:
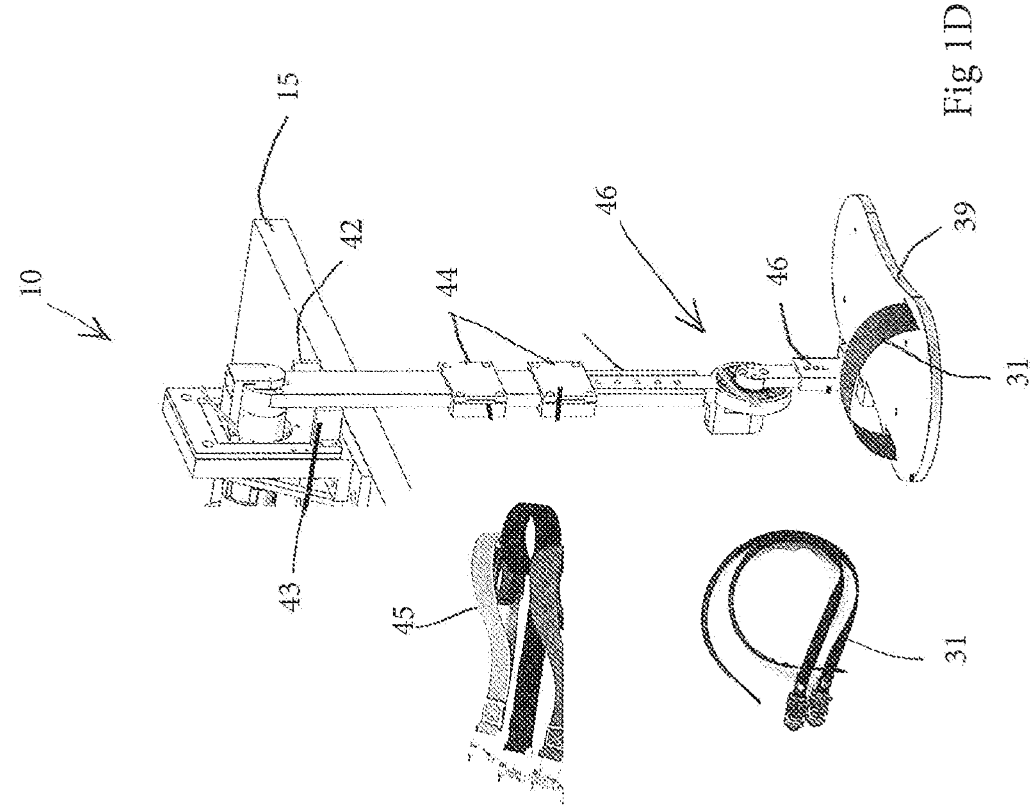
FIG. 1D is a perspective view of a lower leg section of the Exoskeletal System affixed to a testbench.
Figure 1C:
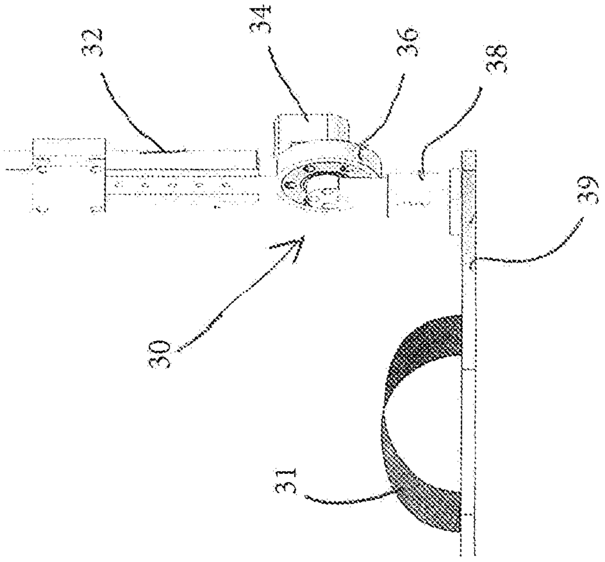
FIG. 1C is a perspective view of a foot and ankle section of the Exoskeletal System.

FIG. 1C shows the lower leg, ankle, and foot section of the Exoskeletal System. Lower leg member 32 is driven by knee motor 12, etc. (NOT SHOWN, see FIG. 1D.) Ankle exoskeletal joint 30 includes ankle joint member 36 which is linked to ankle magnetic encoder 34. Ankle magnetic encoder 34 functions similarly to knee magnetic encoder 14, measuring the speed and/or the range of motion of the movement of the user's ankle. In the embodiment shown, ankle exoskeletal joint 30 is not power-driven, though a power source could be included in an alternate embodiment. The user's foot rests on foot plate 39, secured with foot belt 31. Foot plate 39 is attached to the Exoskeletal System by ankle member 38. In the embodiment shown, the effective length of both lower leg member 32 and ankle member 38 can be adjusted by means of holes and pins, screws, clamps, ratchets, or any other reasonable means.

FIG. 1D shows the entire embodiment of the Exoskeletal System as configured above, affixed to testbench 15 for stationary use. Rear motion limiter 42 and front motion limiter 43 are attached to knee exoskeletal joint 10 in such a way as to prevent hyperextension of the user's knee and otherwise limit the range of motion of the user's knees as appropriate. Leg belts 45 attach the user's lower leg to lower leg member 32, securing it to the user in association with foot belt 31.

When the knee motor (See FIG. 1A) is energized, from the position shown, the lower leg member 32 will pivot forward and up, lifting the lower leg, ankle, and foot sections of the Exoskeletal System. The knee motor can also be energized in the opposite direction to provide resistance to movement for therapeutic reasons. Once the lower leg, ankle, and foot sections of the Exoskeletal System reach either a desired forward level or front motion limiter 43, the process is reversed, with the knee motor bringing the user's lower leg, foot, and ankle, back to the position shown, with the motion monitored by the knee magnetic encoder (See FIG. 1A) and the ankle magnetic encoder (See FIG. 1C.)

Figure 2:
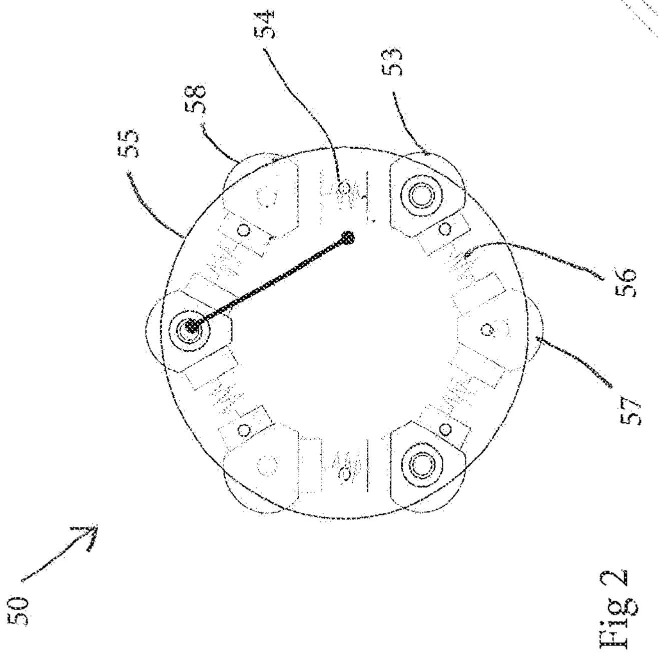
FIG. 2 is an overhead view of an abstracted Series Elastic Actuator element of the Exoskeletal System.

FIG. 2 shows a series elastic actuator (hereafter, "SEA") 50. This is used in an alternate embodiment of the invention as will be shown. Casing 55 contains multiple rotating elements, e.g., first rotating element 53, second rotating element 57 and third rotating element 58. The rotating elements can pivot around a central point as shown. Each rotating element is linked to the rotating elements on either side of it by compression springs, e.g. first compression spring 54 and second compression spring 56, which link first rotating element 54 to third rotating element 58 and second rotating element 57. This arrangement of compression springs and rotating elements completely circumscribes the perimeter of SEA 50. Alternate embodiments wherein not all connections between the rolling elements are elastic and/or some of the rolling elements are not connected to a rolling element on either side are possible.

As is apparent from the above, the SEA uses axial stiffness from the compression springs to generate rotational compliance. The actual configuration of the SEA's components will vary according to user and use environment, but a reasonable configuration would produce an effective stiffness of 440 Nm/rad. Although a wide variety of configurations of material and component spacing are workable for SEA 50, it is preferred to use the following methodology to configure it, where $\tau_1$ is an input torque and $\tau_l$ is an output torque:

$$\sigma_{passive} = 6\sigma_s(R^2 + r^2/3)(2\cos^2\theta - 1)$$

Where: $\sigma_{passive}$: Effective stiffness of the SEA $\sigma_s$: Spring axial stiffness of the compression springs R: Lever arm length (rotation center to center of compression springs)

r: external radius of compression springs

θ: deflection angle

Figure 3:
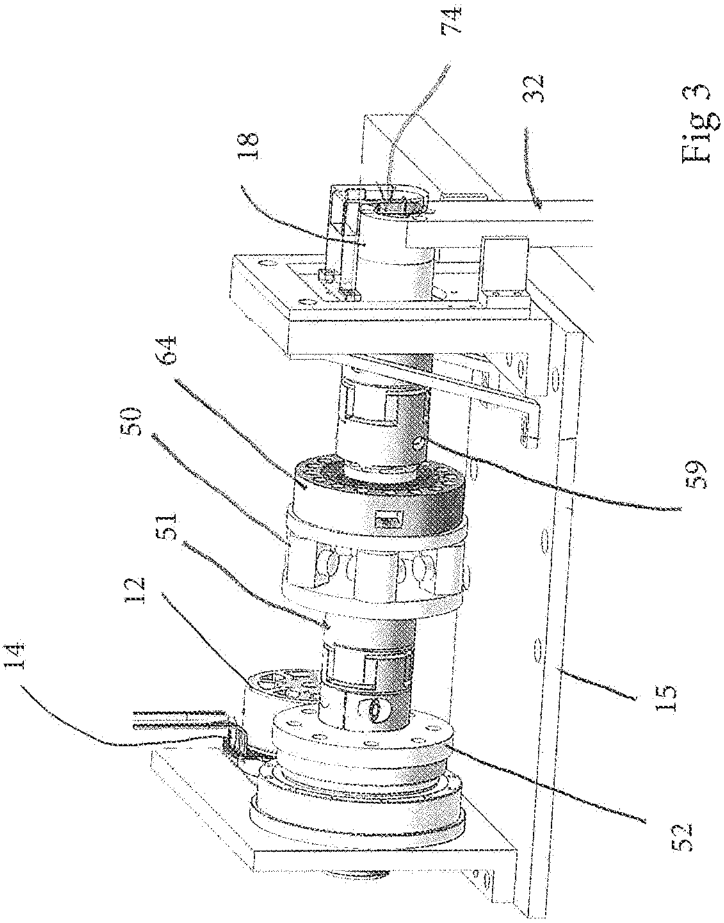
FIG. 3 is a perspective view of an alternate joint element of the Exoskeletal System affixed to a testbench.

FIG. 3 shows the alternate embodiment incorporating the SEA. Knee motor 12, monitored by knee magnetic encoder 14, drives knee harmonic drive 52, which is linked to SEA 50 via first coupling 51. SEA 50 is in turn linked to torque sensor 64, and torque sensor 64 is linked to drive member 18 by second coupling 59. As in the previously described embodiment, drive member 18 then moves lower leg member 32 monitored by second knee magnetic encoder 74.

Figure 5:
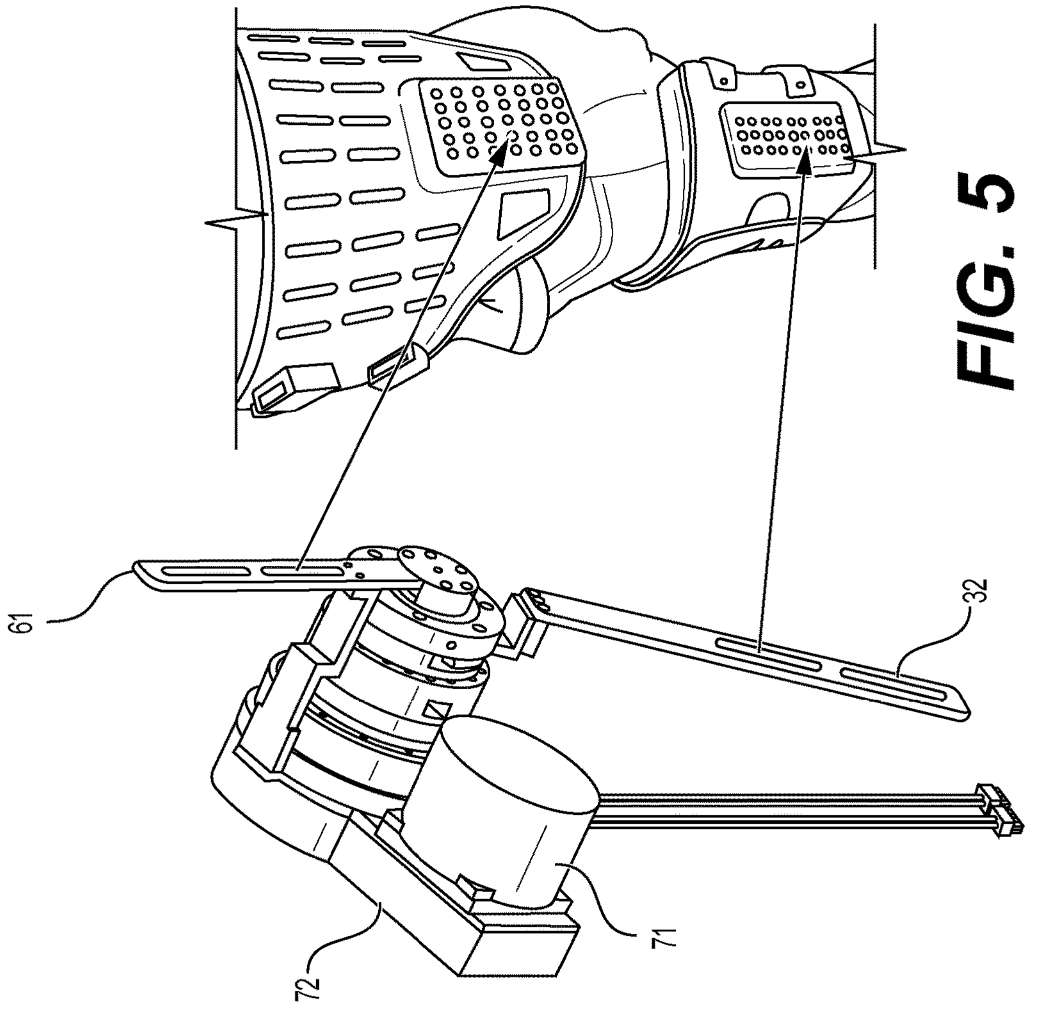
FIG. 5 is a perspective view of a leg section of the Exoskeletal System affixed to a user for use as an orthosis.
Figure 4:
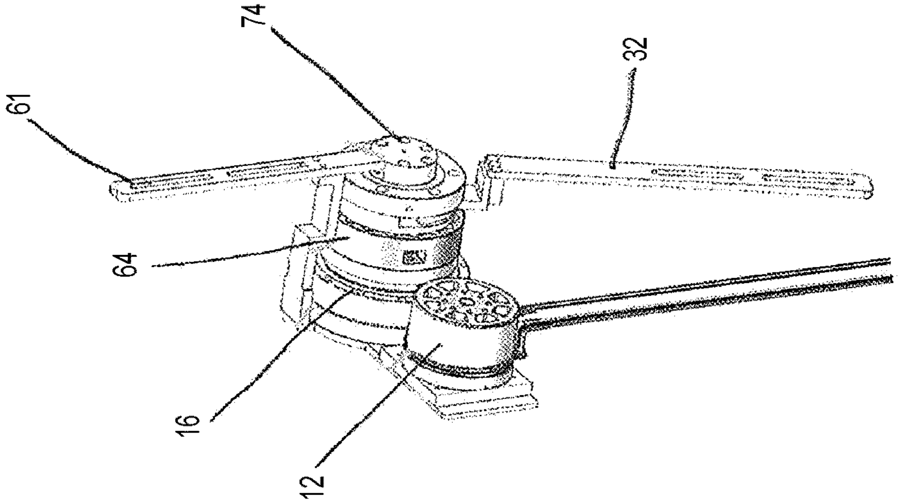
FIG. 4 is a perspective view of a third alternate joint element of the Exoskeletal System.

FIG. 4 shows the second embodiment of the invention assembled for use in the Exoskeletal System as a "hip-knee orthosis." The components of the Exoskeletal System are not affixed to the testbench in preparation for usage as an orthosis (See FIG. 5.) As in prior description, motor 12 drives gearbox 16, which is linked through torque sensor 64 to, ultimately, lower leg member 32, monitored by second knee magnetic encoder 74. Also shown is upper leg member 61, which helps to hold the Exoskeletal System in the proper alignment with the user's leg. (See FIG. 5.)

The first embodiment of the invention is easily convertible to the second, or vice versa, simply by adding the SEA as shown in FIG. 3. This allows the Exoskeletal System to convert quickly and conveniently from a rigid leg-swing configuration to a more compliant orthosis configuration. Additionally, it can be easily configured to allow the Exoskeletal System to act as an outright amplification of the user's own muscle power while maintaining maximum pHRI due to the motion limiters and the moderating effect of the SEA.

FIG. 5 shows the assembled second embodiment of the invention ready to be affixed to the patient's leg. Upper leg clamp 73 will accept upper leg member 61, and lower leg clamp 75 will accept lower leg member 32. The knee motor is covered by knee motor casing 71 and the belt drive linkage is covered by linkage casing 72 for safety and efficiency during mobile usage.

Figure 6:
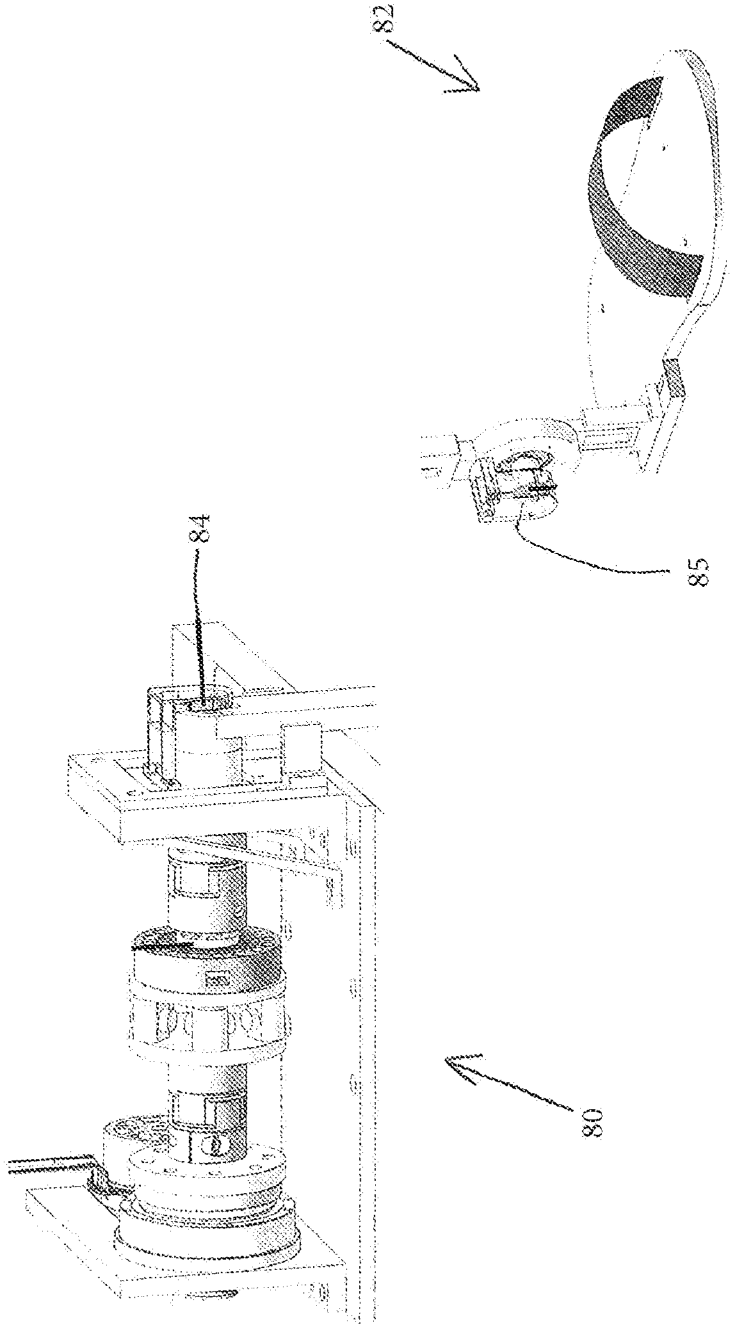
FIG. 6 is a perspective view of a fourth alternate joint element of the Exoskeletal System and a second foot and ankle section of the Exoskeletal System affixed to a testbench.

FIG. 6 shows an alternate embodiment of the invention having the knee exoskeletal joint and ankle exoskeletal joints with the magnetic encoders in alternate locations. Upper exoskeleton assembly 80 incorporates knee magnetic encoder 84 and ankle assembly 82 incorporates ankle magnetic encoder 85.

With the SEA placed in the motor/member linkage, any spasticity or tremor experienced by the user can be absorbed by the SEA, minimizing the effect of such spasticity or tremor on the user's movement. This also increases the pHRI of the Exoskeletal System as any inadvertent high-torque transient motions of the motors can likewise be absorbed by the SEA.

In a second alternate embodiment (NOT SHOWN) one or more of the magnetic encoders are supplemented or replaced by an impedance monitor which measures impedance across the motor provided by the resistance of the load. This would likewise allow measurement of the speed and/or duration of motions against the impedance of the motor.

This application—taken as a whole with the abstract, specification, and drawings being combined—provides sufficient information for a person having ordinary skill in the art to practice the invention as disclosed herein. Any measures necessary to practice this invention are well within the skill of a person having ordinary skill in this art after that person has made a careful study of this disclosure.

Because of this disclosure and solely because of this disclosure, modification of this device and method can become clear to a person having ordinary skill in this particular art. Such modifications are clearly covered by this disclosure.

Although a few embodiments of the present invention have been shown and described, it would be appreciated by those skilled in the art that changes may be made in this embodiment without departing from the principles and spirit of the invention, the scope of which is defined in the claims and their equivalents. Thus, the breadth and scope of the present invention should not be limited by any of the above exemplary embodiments.

What is claimed is:

1. A combined testbench type and walking type compliant exoskeleton system comprising:

a motor;

a gearbox operably affixed to the motor;

a lower leg member operably affixed to the gearbox via a drive member;

a magnetic encoder operably affixed to one of the motor, the gearbox, the lower leg member, or the drive member, such that the magnetic encoder measures a speed and a range of motion of the lower leg member; and a series elastic actuator operably affixed between the gearbox and the drive member, wherein the motor comprises a brushless DC motor and the gearbox comprises a harmonic drive, wherein the series elastic actuator comprises:

a casing having an interior and an exterior:

at least two rotating elements, each rotating element having two elastic member interfaces, the rotating elements operably affixed to the interior of the casing such that each of the rotating elements are pivotable toward or away from at least one other rotating element; and at least two elastic members wherein the elastic members operably connect the elastic member interfaces of the rotating elements, wherein a torque applied to the exterior of the casing is dampened by the elastic members via the rotating members affixed to the interior of the casing.

2. The combined testbench type and walking type compliant exoskeleton system of claim 1, further comprising a testbench, the combined testbench type and walking type compliant exoskeleton system being operably affixable to the testbench such that the combined testbench type and walking type compliant exoskeleton system are operable when affixed to the testbench or when not affixed to the testbench.

3. The combined testbench type and walking type compliant exoskeleton system of claim 2, further comprising an impedance monitor to measure an impedance of the motor which determines a resistance and/or a motion of a load imposing a load force against the motor.

4. The combined testbench type and walking type compliant exoskeleton system of claim 1, further comprising an impedance monitor to measure an impedance of the motor which determines a resistance and/or a motion of a load imposing a load force against the motor.

5. The combined testbench type and walking type compliant exoskeleton system of claim 1, wherein the elastic members comprise compression springs.

6. The combined testbench type and walking type compliant exoskeleton system of claim 1, wherein each of the elastic members comprises a solid piece of an elastic material.

7. The combined testbench type and walking type compliant exoskeleton system of claim 1, wherein the series elastic actuator is removable and the gearbox rigidly is affixed to the leg member without otherwise changing the operation of the combined testbench type and walking type compliant exoskeleton system.

8. The combined testbench type and walking type compliant exoskeleton system of claim 1, wherein the series elastic actuator is removable and the gearbox is rigidly affixed to the leg member without otherwise changing the operation of the combined testbench type and walking type compliant exoskeleton system.

9. A combined testbench type and walking type compliant exoskeleton system comprising:

a motor;

a gearbox operably affixed to the motor;

a lower leg member operably affixed to the gearbox via a drive member; and a magnetic encoder operably affixed to one of the motor, the gearbox, the lower leg member, or the drive member, such that the magnetic encoder measures a speed and a range of motion of the lower leg member:

a testbench; and a series elastic actuator, operably affixed between the gearbox and the drive member, wherein the motor comprises a brushless DC motor and the gearbox comprises a harmonic drive, wherein the combined testbench type and walking type compliant exoskeleton system are operably affixable to the testbench such that the combined testbench type and walking type compliant exoskeleton system are operable when affixed to the testbench or when not affixed to the testbench.

10. The combined testbench type and walking type compliant exoskeleton system of claim 9, wherein the series elastic actuator comprises:

a casing having an interior and an exterior;

at least two rotating elements, each rotating element having first and second elastic member interfaces, the rotating elements operably affixed to the interior of the casing such that each of the rotating elements are pivotable toward or away from at least one other rotating element;

at least two elastic members, such that the elastic members operably connect the elastic member interfaces of the rotating elements, wherein a torque applied to the exterior of the casing is dampened by the elastic members via the rotating members affixed to the interior of the casing.

11. The combined testbench type and walking type compliant exoskeleton system of claim 10, wherein the elastic members comprise compression springs.

12. The combined testbench type and walking type compliant exoskeleton system of claim 10, wherein each of the elastic members comprises a solid piece of an elastic material.

13. The combined testbench type and walking type compliant exoskeleton system of claim 10, wherein the series elastic actuator is removable and the gearbox rigidly is affixed to the leg member without otherwise changing the operation of the combined testbench type and walking type compliant exoskeleton system.

14. The combined testbench type and walking type compliant exoskeleton system of claim 9, wherein the series elastic actuator is removable and the gearbox rigidly is affixed to the leg member without otherwise changing the operation of the combined testbench type and walking type compliant exoskeleton system.

15. A combined testbench type and walking type compliant exoskeleton system comprising:

a motor;

a gearbox operably affixed to the motor;

a lower leg member operably affixed to the gearbox via a drive member;

a series elastic actuator casing having an interior and an exterior;

at least two rotating elements, each rotating element having first and second elastic member interfaces, the rotating elements operably affixed to the interior of the series elastic actuator casing such that each of the rotating elements are pivotable toward or away from at least one other rotating element; and at least two elastic members, such that the elastic members operably connect the elastic member interfaces of the rotating elements, wherein a torque applied to the exterior of the casing by any of the motor, the gearbox, the drive member, or the lower leg member is dampened by the elastic members via the rotating members affixed to the interior of the casing.

16. The combined testbench type and walking type compliant exoskeleton system of claim 15, wherein the series elastic actuator is removable and the gearbox rigidly is affixed to the leg member without otherwise changing the operation of the combined testbench type and walking type compliant exoskeleton system.

17. The combined testbench type and walking type compliant exoskeleton system of claim 15, further comprising an impedance monitor to measure an impedance of the motor which determines a resistance and/or a motion of a load imposing a load force against the motor.

* * * * *